(12) United States Patent
Guo et al.

(10) Patent No.: US 10,959,714 B2
(45) Date of Patent: Mar. 30, 2021

(54) DUAL SYRINGE CARTRIDGE AND HOUSING

(71) Applicant: Ethicon, Inc., Somerville, NJ (US)

(72) Inventors: Jianxin Guo, Livingston, NJ (US);
Jared Schneider, Union, NJ (US);
Simon Cohn, Lebanon, NJ (US);
Christopher Anthony Kokinelis, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 95 days.

(21) Appl. No.: 15/957,118

(22) Filed: Apr. 19, 2018

(65) Prior Publication Data

US 2019/0321021 A1    Oct. 24, 2019

(51) Int. Cl.
| | |
|---|---|
| *A61B 17/00* | (2006.01) |
| *A61M 5/19* | (2006.01) |
| *A61M 5/24* | (2006.01) |
| *A61L 24/10* | (2006.01) |
| *A61M 5/315* | (2006.01) |

(52) U.S. Cl.
CPC ...... *A61B 17/00491* (2013.01); *A61L 24/106* (2013.01); *A61L 24/108* (2013.01); *A61M 5/19* (2013.01); *A61M 5/2422* (2013.01); *A61M 5/2448* (2013.01); *A61M 5/31515* (2013.01); *A61B 2017/00495* (2013.01); *A61M 2005/244* (2013.01); *A61M 2005/2414* (2013.01)

(58) Field of Classification Search
CPC ... A61B 17/00491; A61B 2017/00495; A61M 5/31515; A61M 5/2448; A61M 5/2422; A61M 5/19; A61M 2005/2414; A61M 2005/244; A61L 24/108; A61L 24/106
See application file for complete search history.

(56) References Cited

U.S. PATENT DOCUMENTS

| | | | | |
|---|---|---|---|---|
| 4,677,980 | A | * 7/1987 | Reilly | A61M 5/007 128/DIG. 1 |
| 4,689,042 | A | * 8/1987 | Sarnoff | A61M 5/2066 604/136 |
| 4,874,368 | A | 10/1989 | Miller et al. | |
| 4,979,942 | A | * 12/1990 | Wolf | A61B 17/00491 222/137 |
| 5,104,375 | A | 4/1992 | Wolf et al. | |

(Continued)

FOREIGN PATENT DOCUMENTS

| | | |
|---|---|---|
| EP | 2158848 A1 | 3/2010 |
| WO | 2017086807 A1 | 5/2017 |

OTHER PUBLICATIONS

Notification of Transmittal of the International Search Report and the Written Opinion of the International Searching Authority, or the Declaration; International Search Report for related International Application No. PCT/IB2019/053011, dated Sep. 9, 2019, 6 pages.

*Primary Examiner* — Julian W Woo

(57) ABSTRACT

A dispensing device and cartridge for simultaneous delivery and mixing of multiple co-reactive materials, the cartridge having proximal and distal ends, and having an elongated holder body with substantially parallel longitudinal voids. Multiple syringe bodies are disposed parallel within the voids and multiple co-reactive materials are separately disposed in the syringe bodies. The dispensing device also includes a longitudinal housing which is structured and arranged to receive the cartridge.

29 Claims, 10 Drawing Sheets

(56) References Cited

U.S. PATENT DOCUMENTS

| | | | |
|---|---|---|---|
| 5,354,284 A | 10/1994 | Haber et al. | |
| 5,373,684 A * | 12/1994 | Vacca | B65B 3/003 |
| | | | 53/425 |
| 5,582,596 A | 12/1996 | Fukunaga et al. | |
| 5,656,035 A | 8/1997 | Avoy | |
| 5,785,682 A * | 7/1998 | Grabenkort | A61M 5/284 |
| | | | 604/191 |
| 6,585,696 B2 * | 7/2003 | Petersen | A61B 17/00491 |
| | | | 222/391 |
| 6,874,657 B2 * | 4/2005 | Metzner | A61P 7/04 |
| | | | 222/82 |
| 7,468,049 B2 * | 12/2008 | Laveault | A61M 5/19 |
| | | | 604/191 |
| 7,575,131 B2 | 8/2009 | Feinberg et al. | |
| 7,954,672 B2 | 6/2011 | Keller | |
| 8,376,188 B2 | 2/2013 | Manzano Riera | |
| 8,377,507 B2 * | 2/2013 | Wawrzyniak | A61B 17/00491 |
| | | | 427/207.1 |
| 9,301,739 B2 | 4/2016 | Verkaart | |
| 9,486,190 B2 | 11/2016 | Sherman et al. | |
| 9,586,005 B2 | 3/2017 | Steffen | |
| 9,662,676 B2 * | 5/2017 | Kayser | A61M 5/19 |
| 10,231,720 B2 * | 3/2019 | Goodman | A61M 5/31596 |
| 2005/0096588 A1 * | 5/2005 | Hagmann | A61B 17/00491 |
| | | | 604/82 |
| 2011/0282381 A1 | 11/2011 | Cronin et al. | |
| 2014/0058441 A1 | 2/2014 | Tegels et al. | |
| 2016/0067406 A1 | 3/2016 | Goodman et al. | |

* cited by examiner

DUAL SYRINGE CARTRIDGE AND HOUSING

FIELD

Disclosed is a dispensing device for multiple component materials used in medical or surgical procedures.

Environment

In recent years, minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

One example of a common minimally invasive surgery involves laparoscopic surgical procedures. Laparoscopic procedures may be used to treat hernias, colon dysfunctions, gastroesophageal reflux disease, gallbladder disorders, etc. Typically, the patient undergoing the procedures will return home hours after undergoing surgery.

One challenge presented when performing minimally invasive surgical procedures relates to reducing bleeding at a surgical site when control of bleeding by standard surgical techniques, such as suturing, ligature and cautery, is ineffective or impractical. As opposed to conventional surgical procedures, the surgeon's access to the site of the incision is greatly reduced during minimally invasive procedures and conventional techniques for hemostasis may be difficult to effect.

Recently, the use of tissue sealants and other biological adhesive materials has emerged as an alternate technique for hemostasis. Such tissue sealants may include fibrin, which is comprised of co-reactive thrombin and fibrinogen materials, although other multiple component materials are available. Typically, the individual components of the sealant materials are stored in isolated reservoirs. When mixed, these components may coagulate very quickly, yielding a gel within a short period of time, perhaps 10 or 20 seconds. When applied to the exterior of the body, or when considerable access to the application site is possible, the rapid coagulative properties of the tissue sealant are advantageous. However, such fast-acting properties of conventional tissue sealants have presented potential problems of fouling or clogging during application through laparoscopic devices, which typically results in the destruction of the device.

The fibrin sealants used in the above-disclosed procedures are relatively labile and require low temperature storage, such as below about 0° C., to extend their shelf-life. Advantageously, each of the co-reactive materials is stored in separate reservoirs, such as syringes, and are only combined after thawing and delivery into the site of the incision to be closed. Most preferably, the syringes are glass syringes due to the inertness of glass.

The syringes are generally similar in size and can be easily mixed-up, so the separate storage of each component in similar syringes can cause difficulties in not only storage, but also in packing, shipping and when configuring them for delivery of the fibrin sealant in a medical facility. It would be advantageous if the syringes of the co-reactive materials could be selected and loaded prior to cooling, storage and delivery to ensure that they are properly matched.

Thus, there is a need for a cartridge capable of effectively housing at least two, separate glass syringes containing co-reactive components, wherein the housing is suitable for both storage of the syringes/co-reactive materials and for delivery of the materials.

SUMMARY

Presented herein is a cartridge for storage and delivery of multiple co-reactive materials comprising an elongated holder body having substantially parallel longitudinal voids, multiple hollow cylindrical bodies disposed substantially parallel within the longitudinal voids, the multiple co-reactive materials separately disposed in the multiple hollow cylindrical bodies, wherein the multiple hollow cylindrical bodies have open proximal ends, nozzles at distal ends thereof, and pistons positioned inside, the pistons sealing the open proximal end and slidably moveable within the hollow cylindrical bodies and having no plungers attached.

In one form, the cartridge can further comprise removable closure caps sealing the nozzles, and optionally a removable rear closure cap having substantially parallel plugs fitting into the open proximal ends of the multiple hollow cylindrical bodies.

In another form, the open proximal ends have diameters substantially the same as inner diameters of the hollow cylindrical bodies, and the nozzles have Luer tapers.

Advantageously, the hollow cylindrical bodies are glass syringe bodies, and the co-reactive materials are fibrinogen and thrombin.

In one form, the holder body comprises windows into each of the substantially parallel longitudinal voids.

In another form, the holder body comprises a longitudinal groove between the substantially parallel longitudinal voids.

Also presented is a dispensing device for simultaneous delivery and mixing of multiple co-reactive materials, comprising a cartridge having proximal and distal ends, the cartridge comprising an elongated holder body having substantially parallel longitudinal voids, multiple hollow cylindrical bodies disposed substantially parallel within the longitudinal voids, the multiple co-reactive materials separately disposed in the multiple hollow cylindrical bodies, wherein the multiple hollow cylindrical bodies have open proximal ends, nozzles having Luer tapers at distal ends thereof, and pistons positioned inside, the pistons sealing the open proximal ends and slidably moveable within the hollow cylindrical bodies and having no plungers attached, and a longitudinal housing having proximal and distal ends, structured and arranged to receive the cartridge, having plungers on the proximal end of the longitudinal housing, structured and arranged to contact proximal ends of said pistons.

In one form, the dispensing device further comprises a reactive material receiver having substantially parallel inlet ports a first axial distance apart, located at a distal end of the housing, said inlet ports having co-acting Luer tapers with those of said cylindrical body nozzles.

In another form, the reactive material receiver has substantially parallel exit ports a second axial distance apart and located distal to the inlet ports, and exit nozzles in fluid communication with the exit ports, wherein the second axial distance is different from the first axial distance.

In another form, the dispensing device further comprises a spray or drip mixing tip connected to the exit ports of the reactive material receiver, the mixing tip in fluid communication with the multiple hollow cylindrical bodies of the cartridge through channels within the reactive material receiver and the nozzles.

In yet another form, the longitudinal housing comprises a backbone portion having proximal and distal ends and longitudinal voids on either side of the backbone portion in a side portion of the housing, structured and arranged to accommodate the cartridge between the proximal and distal ends of the housing.

In another form, the longitudinal housing further comprises a clamp to hold the cartridge in the longitudinal void and bias the cartridge and nozzles toward the distal end of the housing, and a fixture at the proximal end of the housing in which the plungers are slidably captive.

In one form, the longitudinal housing comprises an elongated body, wherein the proximal end of the housing is open to receive the cartridge, and a hinged cover for the open proximal end of the housing, wherein said plungers are slidably captive in said hinged cover.

In this form, the hinged cover further comprises a locking tab structured and arranged to engage the proximal end of the housing and lock the cartridge within the housing.

In another form, an inner surface of the hinged cover further comprises one or more spring members for biasing the cartridge toward the distal end of the housing upon closure of the hinged cover, and an extractor hook to assist removal of the cartridge.

In another form, the dispensing device further comprises a reactive material receiver connected to the distal end of the housing with a central stabilizing rod extending from the reactive material receiver into an opening in either the housing or the cartridge, the central stabilizing rod having a nut which engages a thread surrounding the opening.

In this form, the reactive material receiver further comprises substantially parallel inlet ports having Luer tapers which coact with Luer tapers of the nozzles, and the combination of the Luer nut and Luer thread biases the nozzles into a sealing relationship with the inlet ports.

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Figure 1:
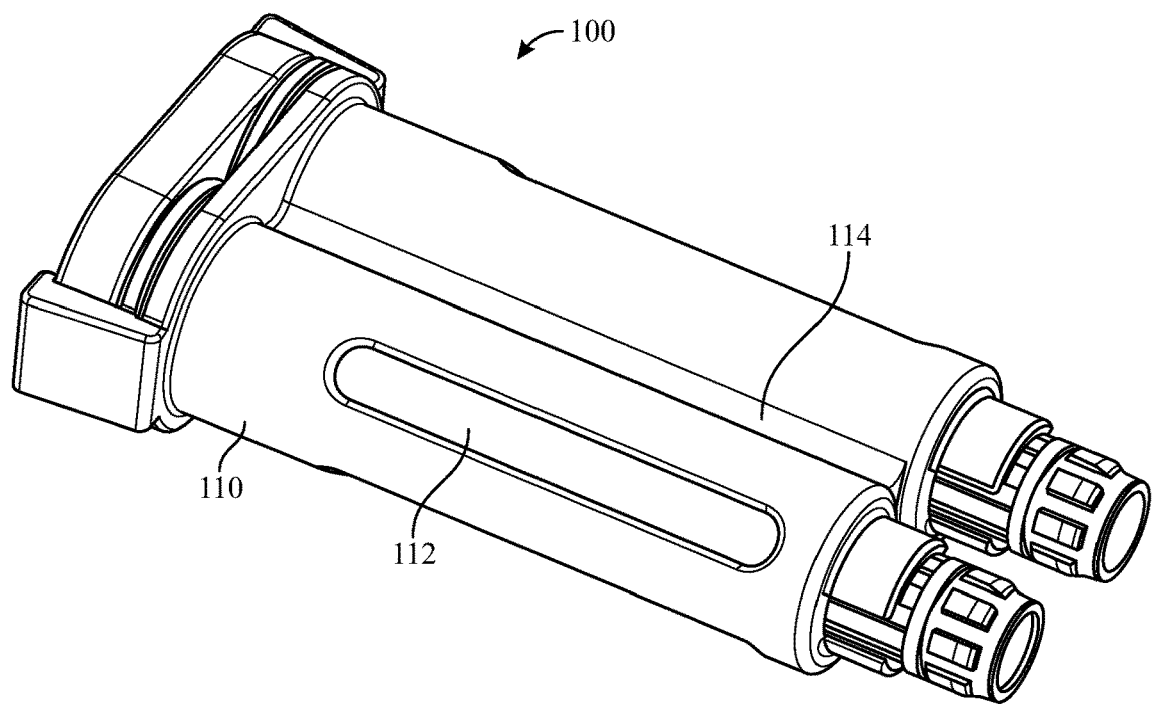
FIG. 1 is a perspective view of a cartridge according to the present application.

Described herein is a medical device which is a cartridge for holding liquid delivery syringes, especially glass syringes, and a housing for receiving the cartridge.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

The term "distal" refers to that end of a device or component which is closest to the dispensing end. The term "proximal" refers to that end of a device or component which is furthest away from the dispensing end.

As used herein the term "substantially parallel" when applied to elements of the disclosed article is intended to mean that the elements are close to but not necessarily perfectly parallel. For example the elements can be disposed at slight angles relative to one another, so long as they are confined within an overlying structure in which they are disposed.

Presented herein is a cartridge for storage and delivery of multiple co-reactive materials to a surgical site, such as an incision requiring sealing. In particular, the incision site can be one which is difficult to seal by conventional suturing, and instead requires use of a biological sealant. One well-known sealant is fibrin, which is formed when fibrinogen and thrombin are combined. While they are naturally occurring in vivo, these two co-reactive materials are commercially available as isolated materials, and can be stored and delivered to medical professionals for later mixing and use in sealing incisions, wounds or the like.

Long term storage of fibrin sealant is complicated by the fact that both the polymerizable material (fibrinogen) and the initiator or accelerator (thrombin) are biological materials and are relatively labile. Long term storage is facilitated by maintaining the temperature of the materials at or below freezing (0° C.), as well as storing them in glass, well-known to be very inert and resistant to gas permeation. Accordingly, fibrinogen and thrombin have become commercially available frozen and stored or packaged in glass syringe bodies.

Additionally, cold storage shipping is relatively expensive, and cold storage space in facilities can be limited. The presently disclosed cartridge system limits the volume of the package that needs to be in cold storage. Further, if more than one unit of biologics is needed in a procedure (as is sometimes the case), the application device can be reloaded with another cartridge rather than obtaining a new device, thus reducing waste.

However, the use of glass syringes to deliver these co-reactive materials to cooperating medical apparatuses, such as manifolds and mixing tips, is complicated by the fact that tolerances on the Luer fittings thereof are often not tight enough to prevent leakage. Additionally, manipulating glass syringes in operating theaters is difficult. Advantageously, sealing of the Luer tapered nozzles to other apparatuses can be accomplished with a press fit between the glass nozzle and the corresponding receiving Luer taper. The presently disclosed apparatus achieves this press fit by use of biasing means other than Luer nuts on the nozzles, to create a sealing force between the glass nozzles and the receiving Luer tapers of the accompanying apparatus(es). This system minimizes the handling of glass syringes and maximizes the ease of their preparation and use.

Additionally, the selection and use of frozen glass syringes in a medical facility can present problems. Condensation on the cold glass can render the syringes slippery and prone to dropping and fracturing. Also, the necessity of selecting syringes filled with different materials from bulk storage could result in mismatching of syringes, requiring disposal of the mismatched pair and restart of the sealing procedure. According to the present disclosure, a cartridge apparatus is provided in which previously matched syringes of the differing materials are inserted and held into the cartridge prior to storage and shipment from the manufacturing facility. The subsequently frozen and delivered cartridge is more easily manipulated in the medical facility, reducing the chance of breakage and mismatching of components. Conveniently, the cartridge is structured and arranged to be received in a dedicated dispensing device, from which the co-reactive materials can be dispensed to downstream devices without leakage.

Figure 2:
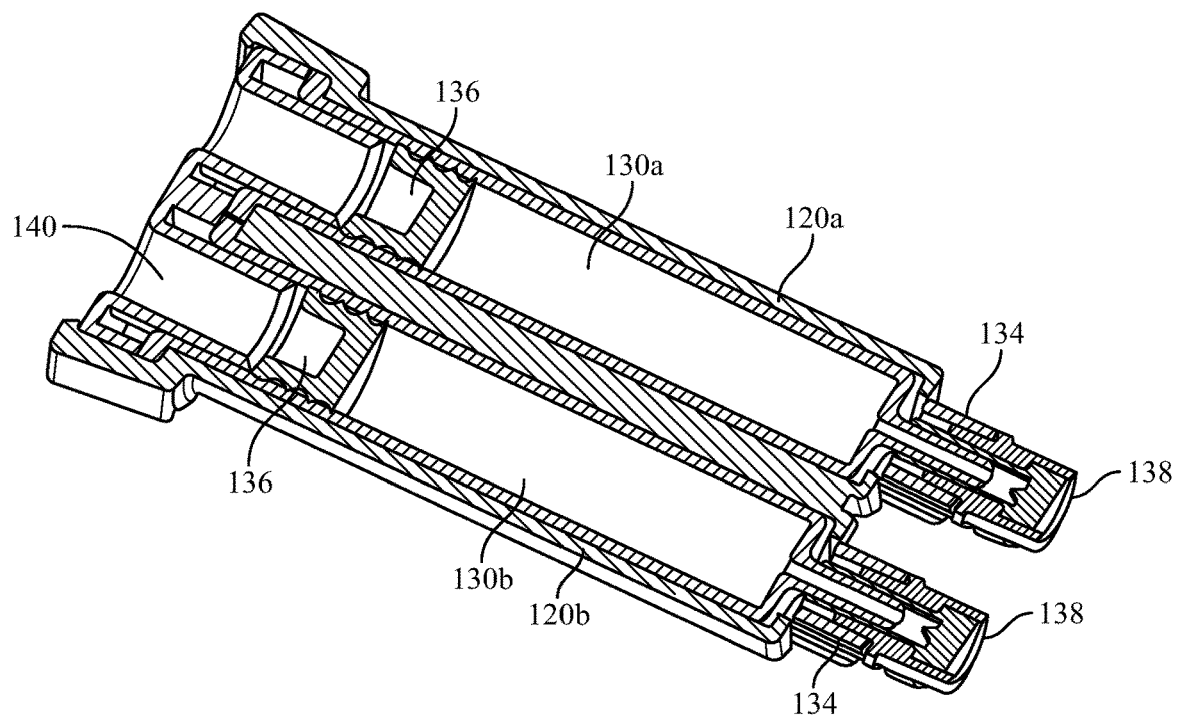
FIG. 2 is a cross-sectional view of the cartridge of FIG. 1.
Figure 3:
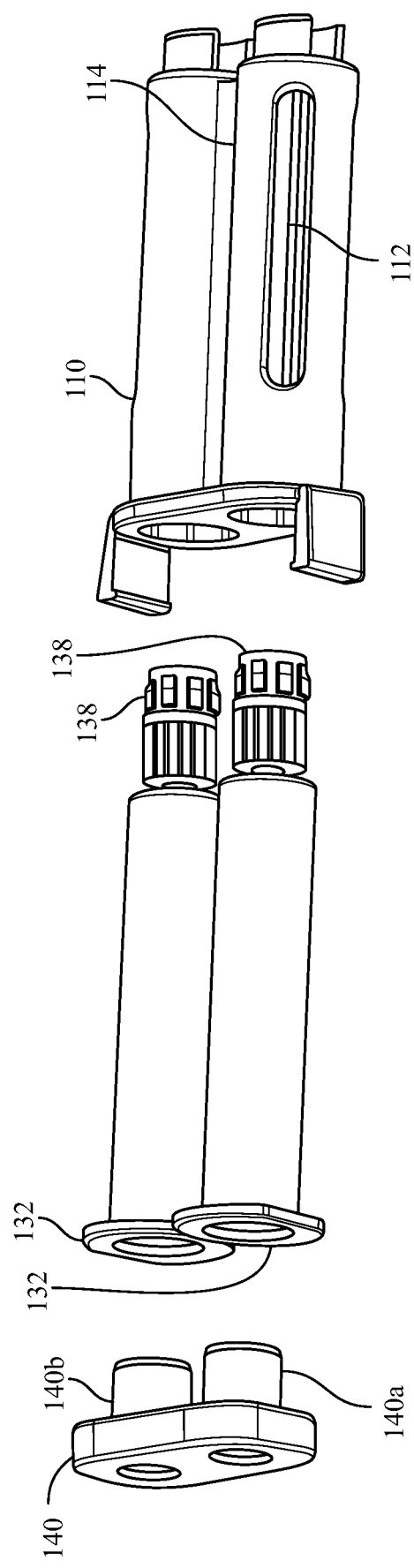
FIG. 3 is an exploded view of the cartridge of FIG. 1.

FIGS. 1-3 illustrate the presently disclosed cartridge 100 which has an elongated holder body 110 having substantially parallel longitudinal voids 120a, 120b, first and second hollow cylindrical bodies 130a, 130b, such as syringes, disposed substantially parallel within the longitudinal voids 120a, 120b. Two co-reactive materials (e.g. thrombin and fibrinogen) are separately disposed in the first and second syringes 130a, 130b, which have open proximal ends 132, nozzles 134 having Luer tapers at distal ends thereof, and pistons 136 positioned inside, the pistons sealing the open proximal end 132 and slidably moveable within the syringes. While being structured to receive plungers on their proximal ends, the pistons have no plungers attached. The cartridge can have removable closure caps 138 sealing the nozzles 134 and a removable rear closure cap 140 having substantially parallel plugs 140a, 140b, fitting into the open proximal ends 132 of the syringes.

The open proximal ends 132 of the syringes 130a, 130b, have diameters substantially the same as inner diameters of the syringes, and the nozzles 134 have Luer tapers. Advantageously, the syringes are glass and the co-reactive materials are fibrinogen and thrombin. The holder body 110 can have windows 112 in each of side-by-side longitudinal voids 120a, 120b, to facilitate thawing and warming of the co-reactive materials in the syringes, as well as viewing of the contents therein. Also, the holder body includes a longitudinal groove 114 between the substantially parallel longitudinal voids 120a, 120b, which groove helps to guide the cartridge into a dispensing device, described below. The holder body 110 can be made of a medically acceptable flexible plastic or polymer, such as polypropylene or polyethylene terephthalate, and the syringes can be snapped into place within the longitudinal voids.

The cartridge 100 is received into one or more dedicated dispensing devices which are structured and arranged specifically to hold the cartridge.

Figure 4A:
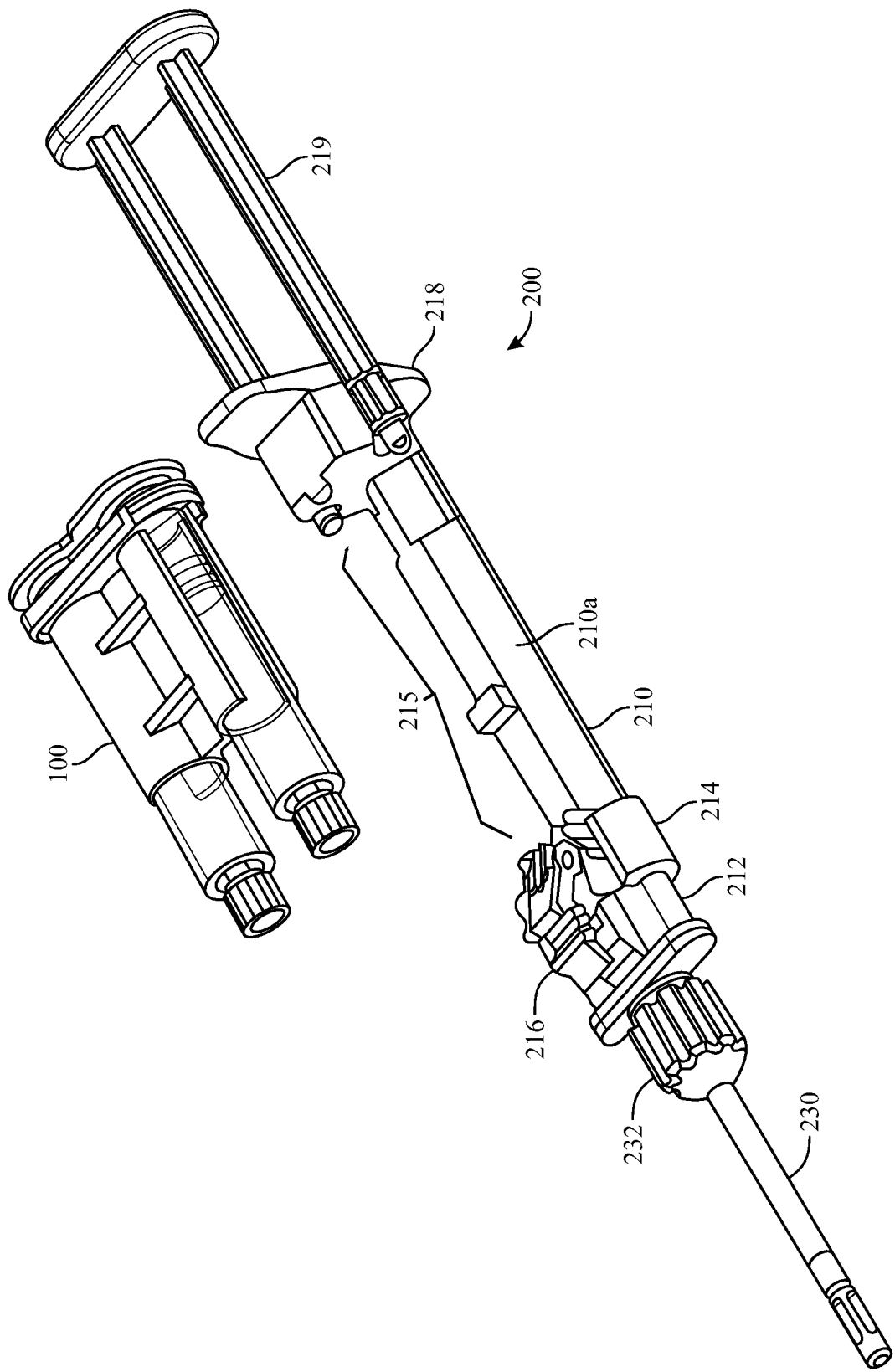
FIG. 4A is an exploded view of a combination of a cartridge and a first embodiment of a longitudinal housing for receiving the cartridge.
Figure 4B:
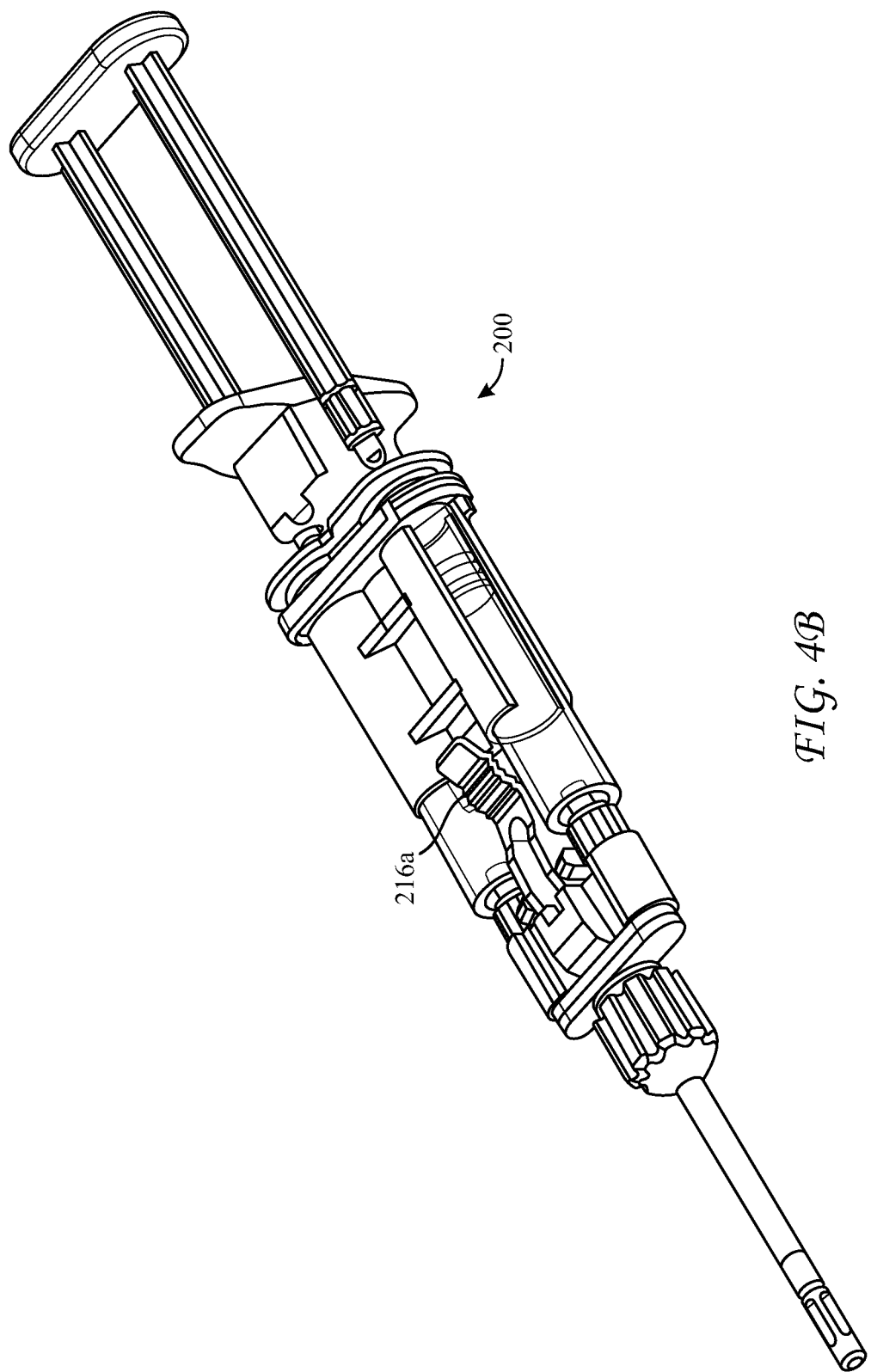
FIG. 4B is an assembled view of the cartridge and housing of FIG. 4A.
Figure 4C:
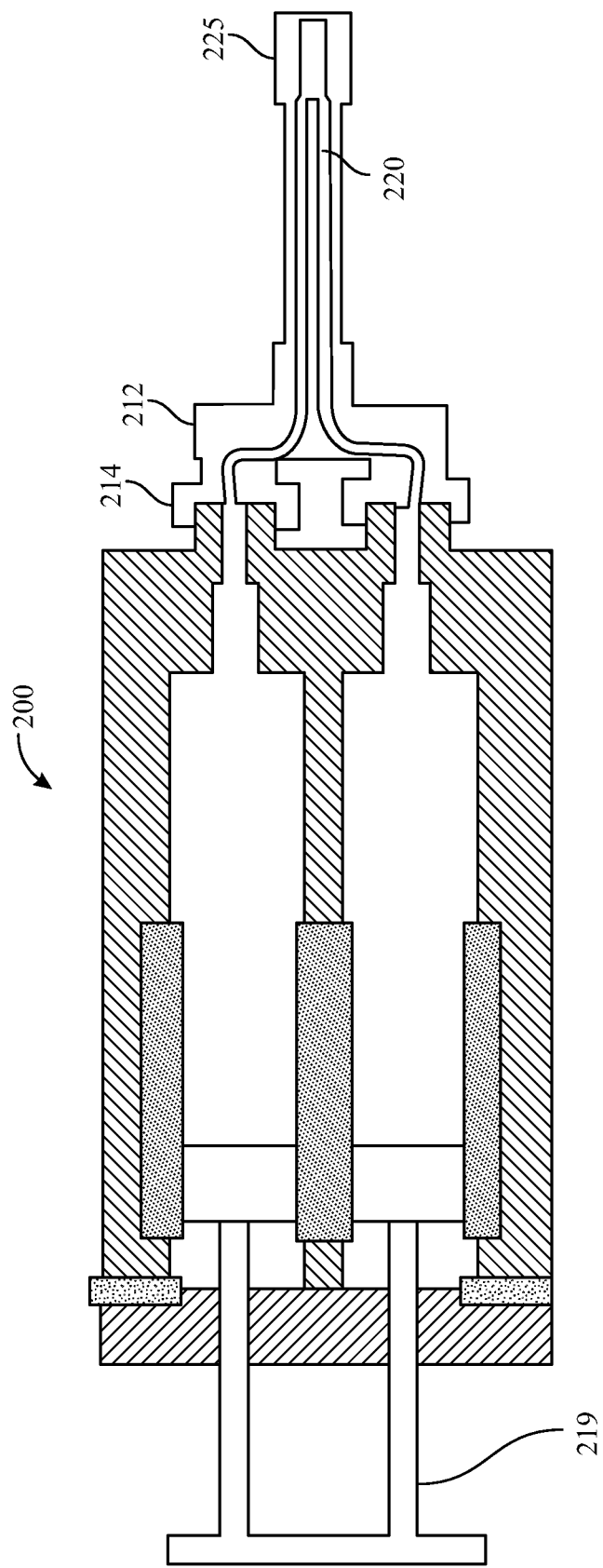
FIG. 4C is a diagrammatic view of the flow path within the assembled cartridge and housing of FIG. 4B.

FIGS. 4A-4C illustrate a top- or side-loading dispensing device 200 for simultaneous delivery and mixing of the two co-reactive materials including a cartridge 100, as described above, and a longitudinal housing 210 including a backbone portion 210a and having proximal and distal ends, the housing being structured and arranged to receive the cartridge 100. The dispensing device 200 can be advantageously made from a medically acceptable flexible plastic or polymer, such as polypropylene or polyethylene terephthalate.

The dispensing device 200 can further comprise a reactive material receiver 212, such as a manifold, either integral with or separate from the longitudinal housing 210. The reactive material receiver has substantially parallel inlet ports 214 having Luer tapers which co-act with those of the hollow cylindrical body nozzles 134, located a first axial distance apart at a distal end of the housing 200, into which the cylindrical body Luer nozzles 134 are seated and sealed. Distal to the inlet ports 214 the reactive material receiver has substantially parallel exit ports 220 a second axial distance apart, wherein the second axial distance is different from the first axial distance, and a Luer nut and thread connector 232 in fluid communication with the exit ports 220. The different first and second axial distances between inlet 214 and exit ports 220 of the reactive material receiver can be configured such that the reactive material receiver 212 adapts the co-reactive material flowpaths from the larger axial distance between syringe nozzles 134 to a smaller axial distance between the adapter's exit ports 220. The dispensing device 200 can further include a spray or drip mixing tip 230 connected at the distal end of the reactive material receiver 212 with the Luer nut and thread connector 232, the mixing tip 230 in fluid communication with the first and second hollow cylindrical bodies 130a, 130b, of the cartridge 100 through the various channels within the reactive material receiver 212 and nozzles 134. The exit ports 220 can be covered with a cap 225 to seal the unit until use.

Additionally, the longitudinal housing 210 has a longitudinal void 215 in a side portion thereof, structured and arranged to accommodate cartridge 100 between the proximal and distal ends of the housing 210. The longitudinal housing further includes a clamp 216 to hold the cartridge 100 in the longitudinal void 215 and to bias the cartridge 100 and thereby the nozzles 134 of the syringes 130a, 130b toward the distal end of the housing and tightly against the inlet ports 214 of the reactive material receiver 212 when the clamp is in the engaged position 216a. In this way the Luer-tapered nozzles 134 of the glass syringes are biased against the co-acting Luer tapers of the inlet ports 214, made of the flexible plastic or polymer, and sealed against leakage of the co-reactive materials. The housing 210 has a fixture 218 at its proximal end which has slidably captive therein substantially parallel plungers 219, structured and arranged to contact the proximal ends of the pistons 136 in the syringes 130a, 130b, held within the cartridge 100. When dispensing of the co-reactive materials is desired, the substantially parallel plungers 219 are pushed into the syringe bodies and against pistons 136, such that the liquefied co-reactive materials are forced through the reactive material receiver 212 and into the spray or drip mixing tip 230.

Figure 4D:
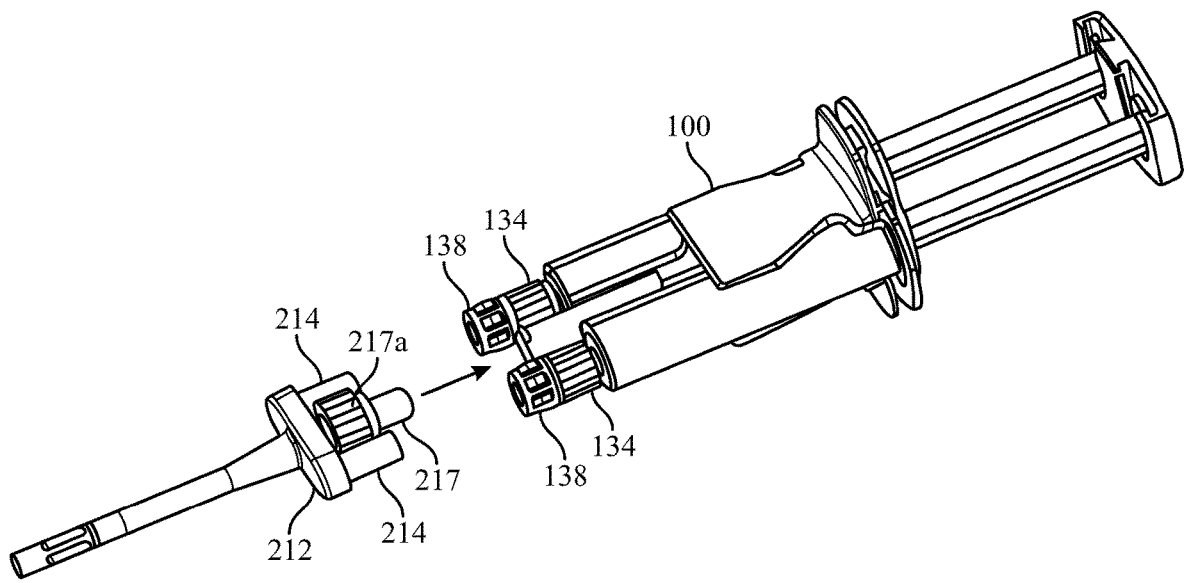
FIGS. 4D and 4E depict an alternative design for biasing syringe nozzles according to FIGS. 4A-4C.
Figure 4E:
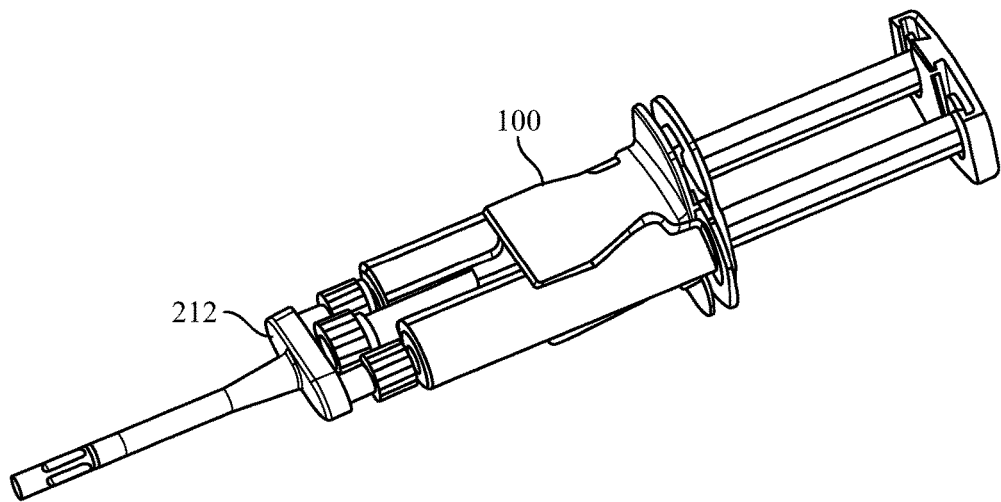
Figure 5A:
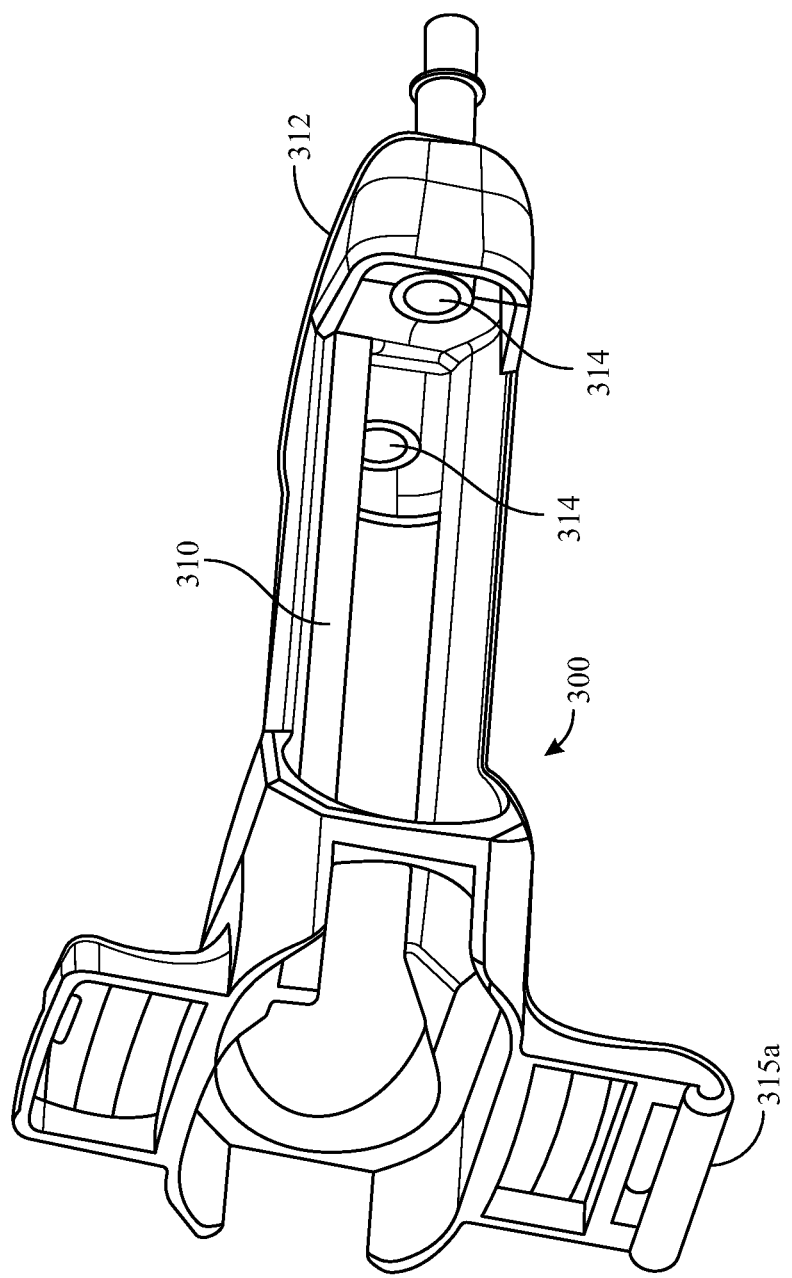
FIG. 5A is a perspective view of a second embodiment of a longitudinal housing for receiving the cartridge of the present application.
Figure 5B:
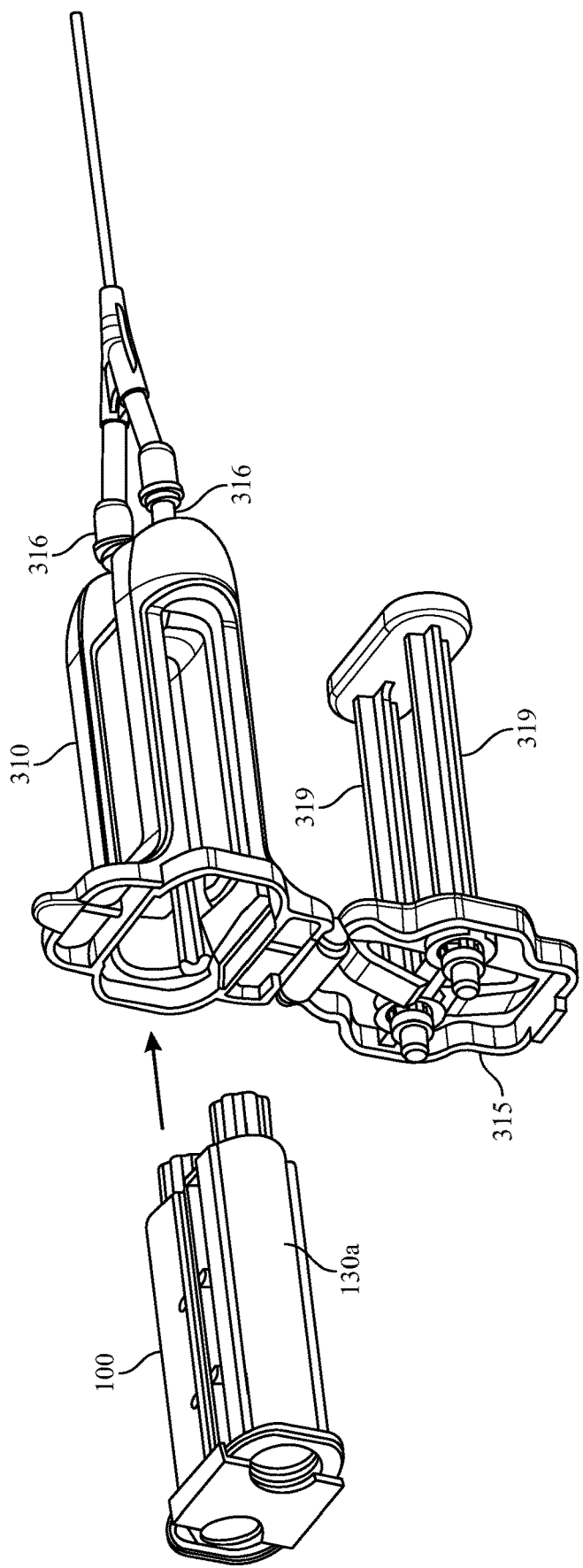
FIG. 5B is an exploded view of a cartridge located proximal to the housing of FIG. 5A.
Figure 5C:
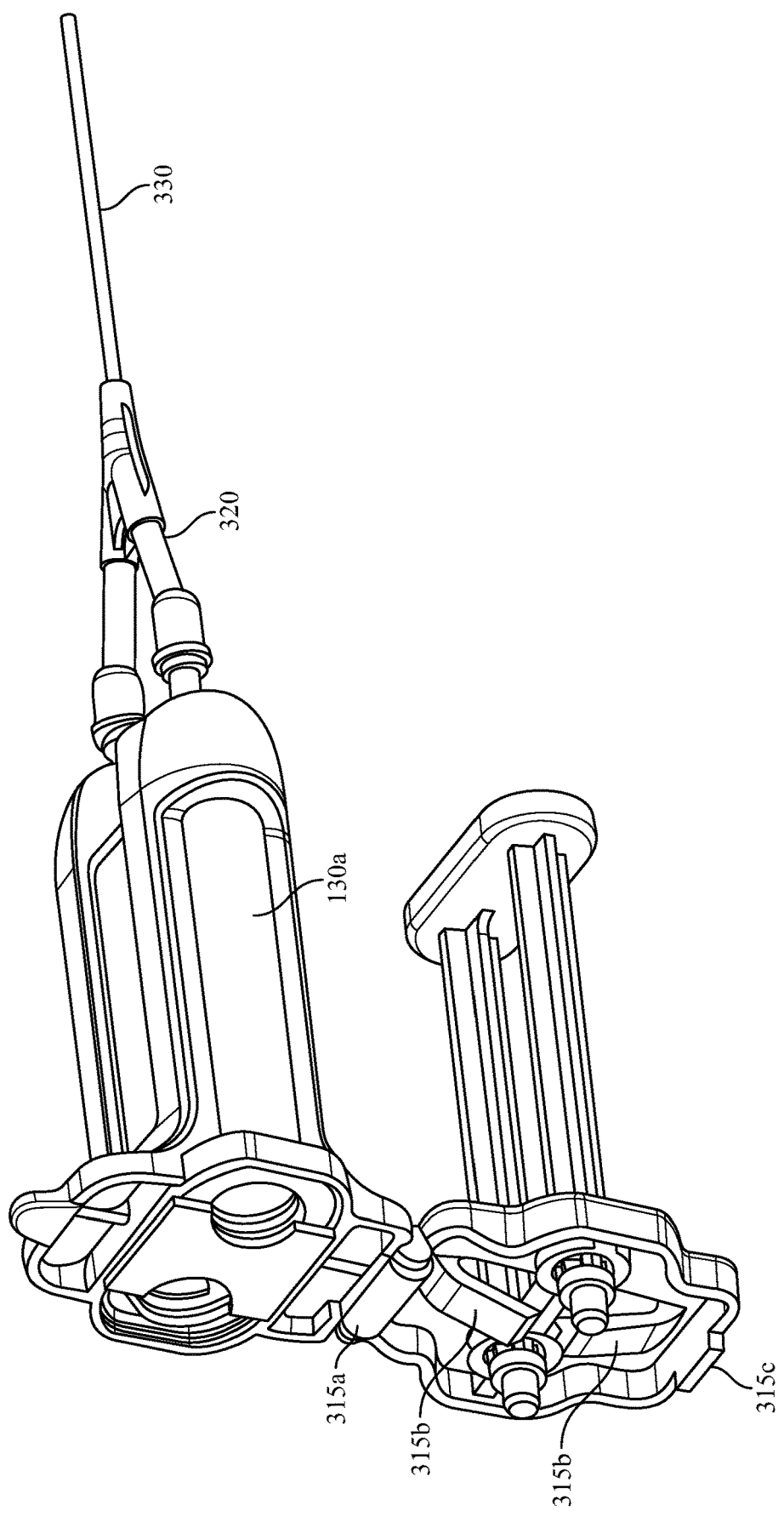
FIGS. 5C and 5D are detailed views of the housing.
Figure 5D:
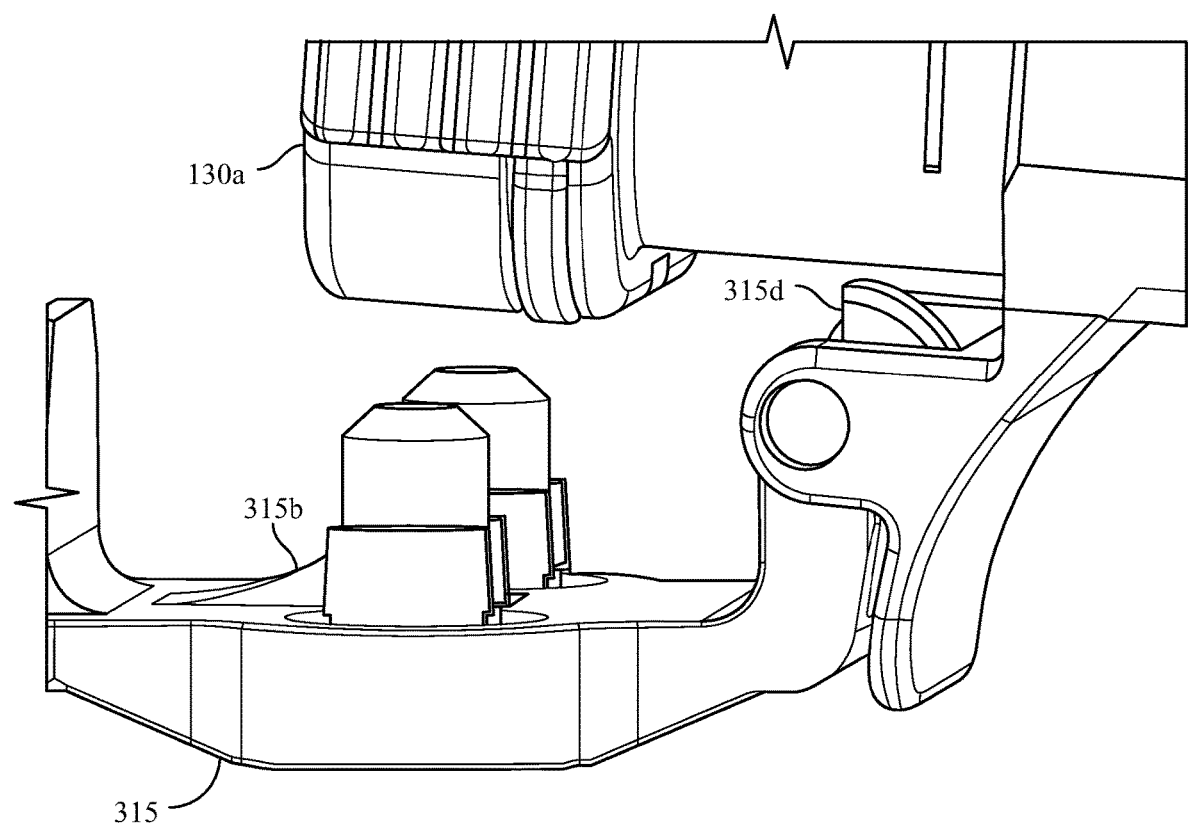

FIGS. 4D-4E depict an alternative design for biasing the syringe nozzles 134 into and against the inlet ports 214 of a reactive material receiver 212 which is separate from the longitudinal housing 210. In this design, the reactive material receiver 212 is provided with a central stabilizing rod 217 which fits into an opening in the cartridge 100 or housing 210. The stabilizing rod 217 is provided with a nut 217a, such as a Luer nut, which when the reactive material receiver is mated with the cartridge 100 or longitudinal housing 210, can be screwed onto a co-acting thread, such as a Luer thread provided around the opening in the cartridge 100 or housing 210.

FIGS. 5A-5D depict an alternative, rear-loading design for the dispensing device 300, wherein the longitudinal housing 310 is an elongated body having proximal and distal ends. The proximal end of the housing 310 is open to receive the cartridge 100, and has a hinged cover 315 connected to the housing at hinge 315a. The hinged cover 315 has slidably captive therein substantially parallel plungers 319 structured and arranged to contact the pistons 136 in the syringe bodies 130a, 130b. The hinged cover 315 further includes a locking tab 315c structured and arranged to engage the proximal end of the housing 310 so as to lock the cartridge 100 into the housing 310. Optionally an inner surface of the hinged cover further comprises one or more spring members, in this case spring tabs 315b, for applying pressure to the distal end of the cartridge 100 upon closure of the hinged cover 315, and an extractor hook 315d to assist removal of the cartridge when the cover is opened. It should be understood that the spring members can also be compression springs, or the like. The extractor hook 315d helps to overcome the friction of the engaged Luer fittings as the hinged cover is opened, rather than requiring a separate action.

The distal end of dispensing device 300 has a reactive material receiver 312 with Luer tapered inlet ports 314 which co-act with Luer tapered nozzles 134 of the glass syringes of the cartridge 100. As can be understood, the spring member(s) 315b compress the cartridge 100 when the hinged door 315 is closed, forcing nozzles 134 to seat and seal in the inlet ports 314. The reactive material receiver likewise can have Luer-type exit ports 316 at its distal end, and is similar to that in the above-described device in that it is configured to adapt the liquid pathway for the co-reactive materials from the axial distance between the exit nozzles 134 of the syringes and a different axial distance between the inlet ports of a manifold 320. Manifold 320 has interior passages which further converge the mutually exclusive co-reactive material passages to a separation sufficient to enter mixing tip 330, wherein the co-reactive materials are mixed immediately prior to delivery to the surgical site.

PCT1. In one form is presented a cartridge for storage and delivery of multiple co-reactive materials comprising an elongated holder body having substantially parallel longitudinal voids, multiple hollow cylindrical bodies disposed substantially parallel within said longitudinal voids, said multiple co-reactive materials separately disposed in said multiple hollow cylindrical bodies. The multiple hollow cylindrical bodies have open proximal ends, nozzles at distal ends thereof, and pistons positioned inside, said pistons sealing the open proximal end and slidably moveable within the hollow cylindrical bodies and having no plungers attached.

PCT2. The cartridge of paragraph PCT1, further comprising removable closure caps sealing the nozzles.

PCT3. The cartridge of paragraph PCT1 or PCT2, further comprising a removable rear closure cap having substantially parallel plugs fitting into the open proximal ends of said multiple hollow cylindrical bodies.

PCT4. The cartridge of any preceding PCT paragraph, wherein the open proximal ends have diameters substantially the same as inner diameters of the hollow cylindrical bodies, and the nozzles have Luer tapers.

PCT5. The cartridge of any preceding PCT paragraph, wherein the hollow cylindrical bodies are glass syringe bodies.

PCT6. The cartridge of any preceding PCT paragraph, wherein said co-reactive materials are fibrinogen and thrombin.

PCT7. The cartridge of any preceding PCT paragraph, wherein the holder body comprises windows into each of the substantially parallel longitudinal voids.

PCT8. The cartridge of any preceding PCT paragraph, wherein the holder body comprises a longitudinal groove between the substantially parallel longitudinal voids.

PCT9. A dispensing device for simultaneous delivery and mixing of multiple co-reactive materials, comprising a cartridge having proximal and distal ends. The cartridge comprises an elongated holder body having substantially parallel longitudinal voids, multiple hollow cylindrical bodies disposed substantially parallel within said longitudinal voids. The multiple co-reactive materials are separately disposed in said multiple hollow cylindrical bodies, wherein the multiple hollow cylindrical bodies have open proximal ends, nozzles having Luer tapers at distal ends thereof, and pistons positioned inside, said pistons sealing the open proximal ends and slidably moveable within the hollow cylindrical bodies and having no plungers attached. The dispensing device also has a longitudinal housing having proximal and distal ends, structured and arranged to receive said cartridge, having plungers on the proximal end of the longitudinal housing, structured and arranged to contact proximal ends of said pistons.

PCT10. The dispensing device of paragraph PCT9, further comprising a reactive material receiver having substantially parallel inlet ports a first axial distance apart, located at a distal end of the housing, said inlet ports having co-acting Luer tapers with those of said cylindrical body nozzles.

PCT11. The dispensing device of paragraph PCT10, wherein the reactive material receiver has substantially parallel exit ports a second axial distance apart and located distal to said inlet ports, and exit nozzles in fluid communication with said exit ports, wherein the second axial distance is different from said first axial distance.

PCT12. The dispensing device of paragraph PCT11, further comprising a spray or drip mixing tip connected to the exit ports of said reactive material receiver, said mixing tip in fluid communication with said multiple hollow cylindrical bodies of said cartridge through channels within the reactive material receiver and the nozzles.

PCT13. The dispensing device of any of paragraphs PCT9 to PCT12, wherein the longitudinal housing comprises a backbone portion having proximal and distal ends and longitudinal voids on either side of said backbone portion in a side portion of said housing, structured and arranged to accommodate said cartridge between said proximal and distal ends of the housing.

PCT14. The dispensing device of paragraph PCT13, wherein the longitudinal housing further comprises a clamp to hold said cartridge in said longitudinal void and bias said cartridge and nozzles toward the distal end of the housing, and a fixture at the proximal end of said housing in which the plungers are slidably captive.

PCT15. The dispensing device of any of paragraphs PCT9 to PCT14, wherein the longitudinal housing comprises an elongated body, wherein the proximal end of said housing is open to receive said cartridge, and a hinged cover for said open proximal end of said housing, wherein said plungers are slidably captive in said hinged cover.

PCT16. The dispensing device of paragraph PCT15, wherein the hinged cover further comprises a locking tab structured and arranged to engage the proximal end of the housing and lock said cartridge within the housing.

PCT17. The dispensing device of paragraph PCT16, wherein an inner surface of the hinged cover further comprises one or more spring members for biasing the cartridge toward the distal end of the housing upon closure of said hinged cover, and an extractor hook to assist removal of the cartridge.

PCT18. The dispensing device of any of paragraphs PCT9 to PCT17, further comprising a reactive material receiver connected to the distal end of the housing with a central stabilizing rod extending from said reactive material receiver into an opening in either the housing or the cartridge, said central stabilizing rod having a nut which engages a thread surrounding the opening.

PCT19. The dispensing device of paragraph PCT18, wherein the reactive material receiver further comprises substantially parallel inlet ports having Luer tapers which co-act with Luer tapers of said nozzles, and the combination of said Luer nut and Luer thread biases said nozzles into a sealing relationship with said inlet ports.

INDUSTRIAL APPLICABILITY

The devices disclosed herein are applicable to the medical field.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and sub-combinations that are directed to one of the disclosed inventions and are novel and non-obvious. Inventions embodied in other combinations and sub-combinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

We claim:

1. A dispensing device for simultaneous delivery and mixing of multiple co-reactive materials, comprising:
    a cartridge having proximal and distal ends, the cartridge comprising:
        an elongated holder body having substantially parallel longitudinal voids, multiple hollow cylindrical bodies disposed substantially parallel within said longitudinal voids, said co-reactive materials separately disposed in said multiple hollow cylindrical bodies, wherein the multiple hollow cylindrical bodies have open proximal ends, nozzles having Luer tapers at distal ends thereof, and pistons positioned inside, said pistons sealing the open proximal ends and slidably moveable within the hollow cylindrical bodies and having no plungers attached;
    a longitudinal housing having proximal and distal ends, structured and arranged to receive said cartridge, having plungers on the proximal end of the longitudinal housing, structured and arranged to contact proximal ends of said pistons; and
    a reactive material receiver connected to the distal end of the housing with a central stabilizing rod extending from said reactive material receiver into an opening in either the housing or the cartridge, said central stabilizing rod having a nut which engages a thread surrounding the opening,
    wherein the reactive material receiver further comprises substantially parallel inlet ports having Luer tapers which co-act with Luer tapers of said nozzles, and a combination of a Luer nut and Luer thread biases said nozzles into a sealing relationship with said inlet ports.

2. The dispensing device of claim 1, further comprising removable closure caps sealing the nozzles.

3. The dispensing device of claim 1, further comprising a removable rear closure cap having plugs fitting into the open proximal ends of said multiple, substantially parallel hollow cylindrical bodies.

4. The dispensing device of claim 1, wherein the open proximal ends have diameters substantially the same as inner diameters of the hollow cylindrical bodies.

5. The dispensing device of claim 1, wherein the hollow cylindrical bodies are glass syringe bodies.

6. The dispensing device of claim 1, wherein said co-reactive materials are fibrinogen and thrombin.

7. The dispensing device of claim 1, wherein the holder body comprises windows into each of the substantially parallel longitudinal voids.

8. The dispensing device of claim 1, wherein the holder body comprises a longitudinal groove between the substantially parallel longitudinal voids.

9. The dispensing device of claim 1, wherein the reactive material receiver inlet ports are a first axial distance apart and located at a distal end of the housing.

10. The dispensing device of claim 9, wherein the reactive material receiver has substantially parallel exit ports a second axial distance apart and located distal to said inlet ports, and exit nozzles in fluid communication with said exit ports, wherein the second axial distance is different from said first axial distance.

11. The dispensing device of claim 9, further comprising a spray or drip mixing tip connected to the exit ports of said reactive material receiver, said mixing tip in fluid communication with said multiple hollow cylindrical bodies of said cartridge through channels within the reactive material receiver and the nozzles.

12. The dispensing device of claim 1, wherein the longitudinal housing comprises a backbone portion having proximal and distal ends and substantially parallel longitudinal voids on either side of said backbone portion in a side portion of said housing, structured and arranged to accommodate said cartridge between said proximal and distal ends of the housing.

13. The dispensing device of claim 11, wherein the longitudinal housing further comprises a clamp to hold said cartridge in said longitudinal void and bias said cartridge and nozzles toward the distal end of the housing, and a fixture at the proximal end of said housing in which the plungers are slidably captive.

14. The dispensing device of claim 1, wherein the longitudinal housing comprises an elongated body, wherein the proximal end of said housing is open to receive said cartridge, and a hinged cover for said open proximal end of said housing, wherein said plungers are slidably captive in said hinged cover.

15. The dispensing device of claim 14, wherein the hinged cover further comprises a locking tab structured and arranged to engage the proximal end of the housing and lock said cartridge within the housing.

16. The dispensing device of claim 15, wherein an inner surface of the hinged cover further comprises one or more spring members for biasing the cartridge toward the distal end of the housing upon closure of said hinged cover, and an extractor hook to assist removal of the cartridge.

17. A dispensing device for simultaneous delivery and mixing of multiple co-reactive materials, comprising:

a cartridge having proximal and distal ends, the cartridge comprising:
an elongated holder body having substantially parallel longitudinal voids, multiple hollow cylindrical bodies disposed substantially parallel within said longitudinal voids, said co-reactive materials separately disposed in said multiple hollow cylindrical bodies, wherein the multiple hollow cylindrical bodies have open proximal ends, nozzles having Luer tapers at distal ends thereof, and pistons positioned inside, said pistons sealing the open proximal ends and slidably moveable within the hollow cylindrical bodies and having no plungers attached; and
a longitudinal housing having proximal and distal ends, structured and arranged to receive said cartridge, having plungers on the proximal end of the longitudinal housing, structured and arranged to contact proximal ends of said pistons,
wherein the longitudinal housing comprises an elongated body, wherein the proximal end of said housing is open to receive said cartridge, and a hinged cover for said open proximal end of said housing, wherein said plungers are slidably captive in said hinged cover,
wherein the hinged cover further comprises a locking tab structured and arranged to engage the proximal end of the housing and lock said cartridge within the housing, and
wherein an inner surface of the hinged cover further comprises one or more spring members for biasing the cartridge toward the distal end of the housing upon closure of said hinged cover, and an extractor hook to assist removal of the cartridge.

18. The dispensing device of claim 17, further comprising removable closure caps sealing the nozzles.

19. The dispensing device of claim 17, further comprising a removable rear closure cap having plugs fitting into the open proximal ends of said multiple, substantially parallel hollow cylindrical bodies.

20. The dispensing device of claim 17, wherein the open proximal ends have diameters substantially the same as inner diameters of the hollow cylindrical bodies.

21. The dispensing device of claim 17, wherein the hollow cylindrical bodies are glass syringe bodies.

22. The dispensing device of claim 17, wherein said co-reactive materials are fibrinogen and thrombin.

23. The dispensing device of claim 17, wherein the holder body comprises windows into each of the substantially parallel longitudinal voids.

24. The dispensing device of claim 17, wherein the holder body comprises a longitudinal groove between the substantially parallel longitudinal voids.

25. The dispensing device of claim 17, wherein the reactive material receiver inlet ports are a first axial distance apart and located at a distal end of the housing.

26. The dispensing device of claim 25, wherein the reactive material receiver has substantially parallel exit ports a second axial distance apart and located distal to said inlet ports, and exit nozzles in fluid communication with said exit ports, wherein the second axial distance is different from said first axial distance.

27. The dispensing device of claim 25, further comprising a spray or drip mixing tip connected to the exit ports of said reactive material receiver, said mixing tip in fluid communication with said multiple hollow cylindrical bodies of said cartridge through channels within the reactive material receiver and the nozzles.

28. The dispensing device of claim 17, wherein the longitudinal housing comprises a backbone portion having proximal and distal ends and substantially parallel longitudinal voids on either side of said backbone portion in a side portion of said housing, structured and arranged to accommodate said cartridge between said proximal and distal ends of the housing.

29. The dispensing device of claim 28, wherein the longitudinal housing further comprises a clamp to hold said cartridge in said longitudinal void and bias said cartridge and nozzles toward the distal end of the housing, and a fixture at the proximal end of said housing in which the plungers are slidably captive.

* * * * *